United States Patent [19]
Loescher et al.

[11] Patent Number: 6,050,552
[45] Date of Patent: Apr. 18, 2000

[54] HUMIDIFIER ASSEMBLY

[75] Inventors: Thomas C. Loescher, Encinitas; Dennis Fitzwater, Murrieta, both of Calif.

[73] Assignee: Hudson Respiratory Care Inc., Temecula, Calif.

[21] Appl. No.: 09/088,553

[22] Filed: Jun. 1, 1998

[51] Int. Cl.$^7$ .................................................. B01F 3/04
[52] U.S. Cl. ........................... 261/129; 261/74; 261/141; 128/203.26; 128/204.14
[58] Field of Search ............................. 261/72.1, 74, 129, 261/141, 142; 128/203.26, 203.27, 203.28, 204.13, 204.14

[56] References Cited

U.S. PATENT DOCUMENTS

| | | | |
|---|---|---|---|
| 552,968 | 1/1896 | Pendry | 128/204.13 |
| 2,085,155 | 6/1937 | Heidbrink | 128/204.13 |
| 3,902,486 | 9/1975 | Guichard | 128/204.13 |
| 3,954,920 | 5/1976 | Heath | 128/203.27 |
| 4,110,419 | 8/1978 | Miller . | |
| 4,172,105 | 10/1979 | Miller et al. . | |
| 4,178,334 | 12/1979 | Miller . | |
| 4,195,044 | 3/1980 | Miller . | |
| 4,366,105 | 12/1982 | Nowacki . | |
| 4,500,480 | 2/1985 | Cambio, Jr. . | |
| 4,564,748 | 1/1986 | Gupton | 128/203.27 |
| 4,606,866 | 8/1986 | McGlothlin et al. | 261/74 |
| 4,652,408 | 3/1987 | Montgomery | 261/142 |
| 4,674,494 | 6/1987 | Wiencek . | |
| 4,676,237 | 6/1987 | Wood et al. | 261/142 |
| 4,708,831 | 11/1987 | Elsworth et al. | 261/142 |
| 4,714,078 | 12/1987 | Paluch | 128/203.17 |
| 4,765,327 | 8/1988 | Shim | 261/142 |
| 4,774,032 | 9/1988 | Coates et al. | 128/204.13 |

FOREIGN PATENT DOCUMENTS 43 03 645A  8/1994  Germany .

*Primary Examiner*—C. Scott Bushey
*Attorney, Agent, or Firm*—Knobbe, Martens, Olson & Bear, LLP

[57] ABSTRACT

A humidifier assembly includes a cartridge secured in the humidification chamber cavity for displacing between about 20% and about 80% of the volume of the cavity.

41 Claims, 3 Drawing Sheets

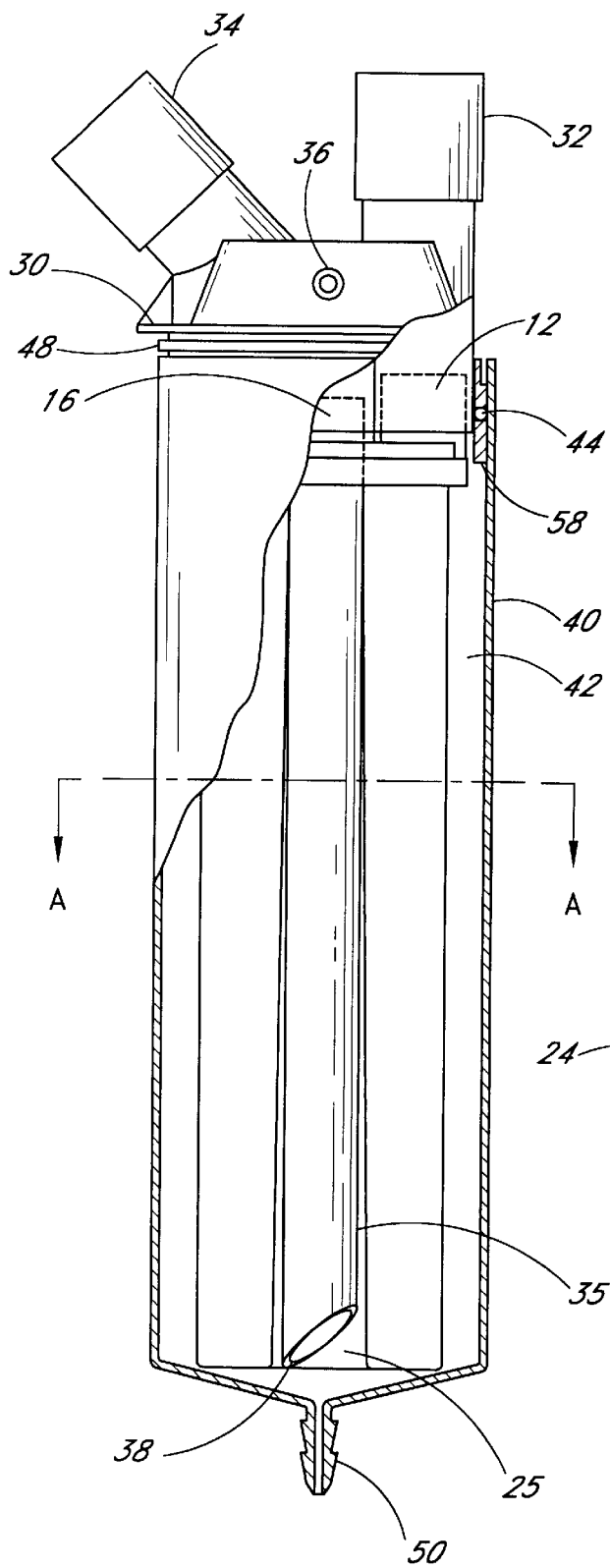
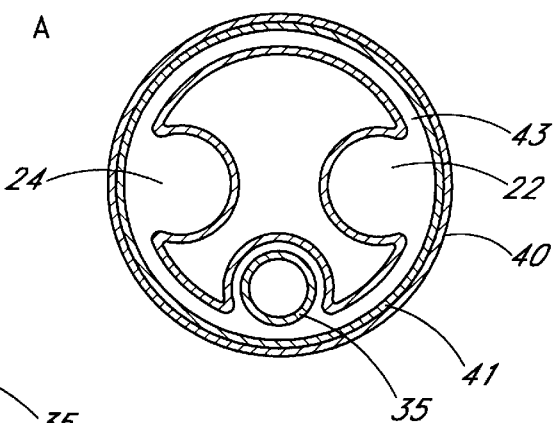
FIG. 4
FIG. 5

6,050,552

1

HUMIDIFIER ASSEMBLY

BACKGROUND OF THE INVENTION

Respiratory therapy systems using mechanical ventilation for moving gas into a patient's lungs commonly incorporate a humidifier along the respiratory circuit in order to humidify the respiratory gas directed to the patient. Examples of such humidifiers are disclosed in U.S. Pat. Nos., 4,110,419, 4,172,105, 4,195,044, 4,500,480 and 4,674,494, the disclosures of which are incorporated herein by reference. Such humidifiers utilize a cartridge-type humidifier positioned in a heater, with water supplied from a pre-filled sterile water reservoir. Hudson Respiratory Care Inc. markets such a system as CONCHA®. A heater used for heating the cartridge humidifier is described in U.S. Pat. No. 4,564,748, the description of which is incorporated herein by reference. Such an apparatus provides heated humidification to be delivered to the patient during mechanical ventilation therapy.

In mechanical ventilation, a ventilator forces respiratory gas along the ventilation circuit tubing into the patient's lungs. When mechanical ventilation therapy is prescribed to children, infants and neonates it is desirable to limit the amount of pressure delivered to the patient so that injury to the lung may be avoided. The pressure required to deliver the prescribed amount of gas to the patient is dependent upon the resistance and compliance characteristics of the patient's lungs, as well as the compliance or volume of gas in the respiratory circuit between the ventilator and the patient. Thus, the compressible volume of gas inside the humidifier chamber during the inspiratory phase is an important factor in the delivery of gas to the patient's lungs at the lowest pressure to properly ventilate the patient Where the volume of gas inside the humidifier chamber is substantial, the greater the compliance of the system is, and the more ventilator pressure required to deliver the appropriate amount of gas to the patient so that the blood carbon dioxide level may be appropriately maintained. Although for most adults, high mechanical ventilation pressures are often not of such concern, for pediatric, and particularly neonatal ventilation, relatively low pressure ventilation is of substantial criticality, with lung pressures of under 30 cm $H_2O$ being desirable to prevent lung injury. In order to assure such low-pressure performance, it is desired to effectively reduce the compliance of the humidifier used in the ventilator circuit. It is to such a reduced and improved performance humidifier that the present invention is directed.

SUMMARY OF THE INVENTION

This invention is directed to a humidifier having a humidification chamber for holding water and through which respiratory gas is forced, heated, and humidified and then directed to a patient during respiratory therapy. The humidifier is provided with a cartridge positioned or located in the container cavity where it displaces at least about 20% and up to about 80% of the cavity volume or space which would otherwise be occupied by gas or gas and water in the chamber. In a preferred embodiment, the cartridge is provided with gas inlet and outlet ports and the humidifier assembly includes a cover or lid for the humidifier container. These and other features as well as advantages of the apparatus of the invention and its use will be described hereinafter.

2

Figures 1, 2, 3:
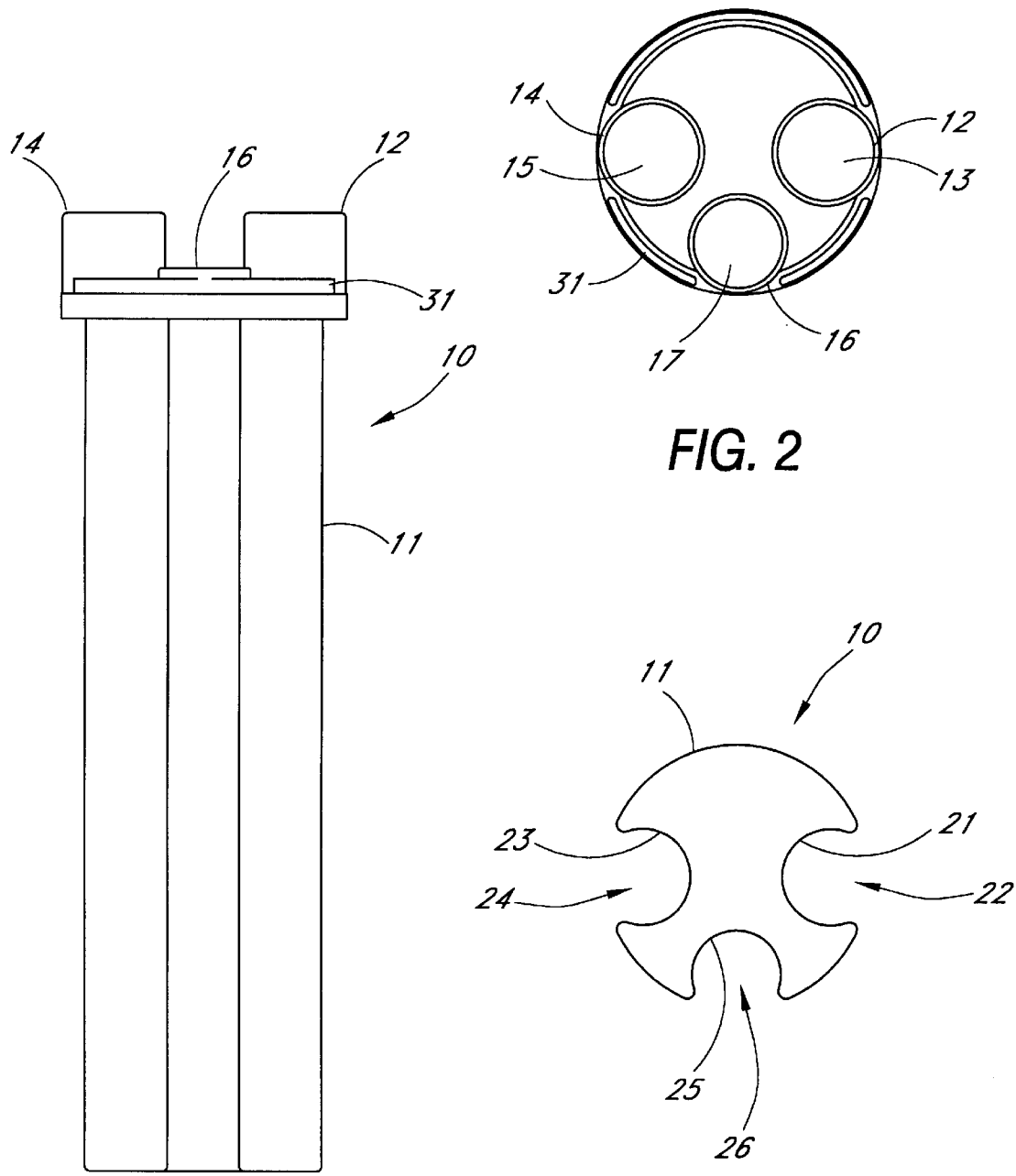
FIG. 1 is a side elevational view of a cartridge for being installed in a humidifier chamber.
Figure 6:
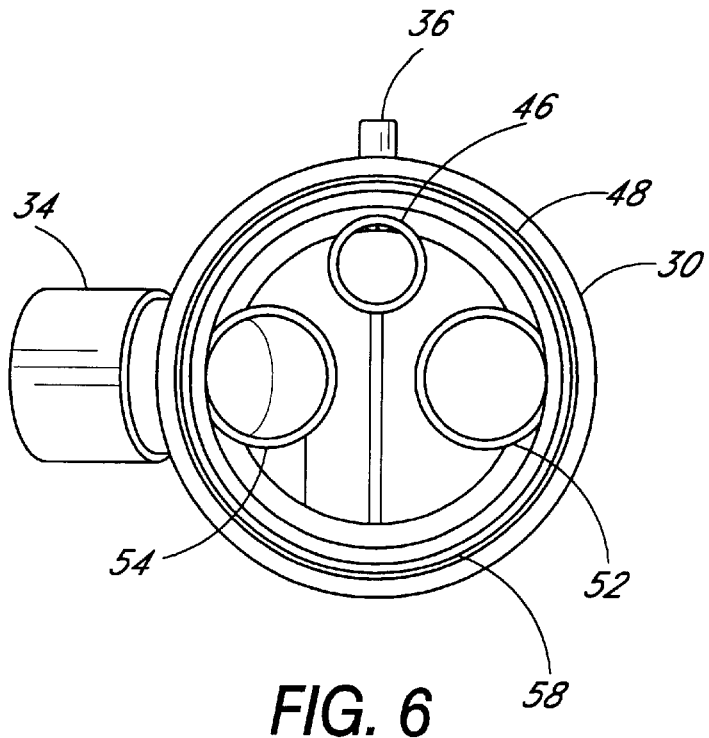
Figure 7:
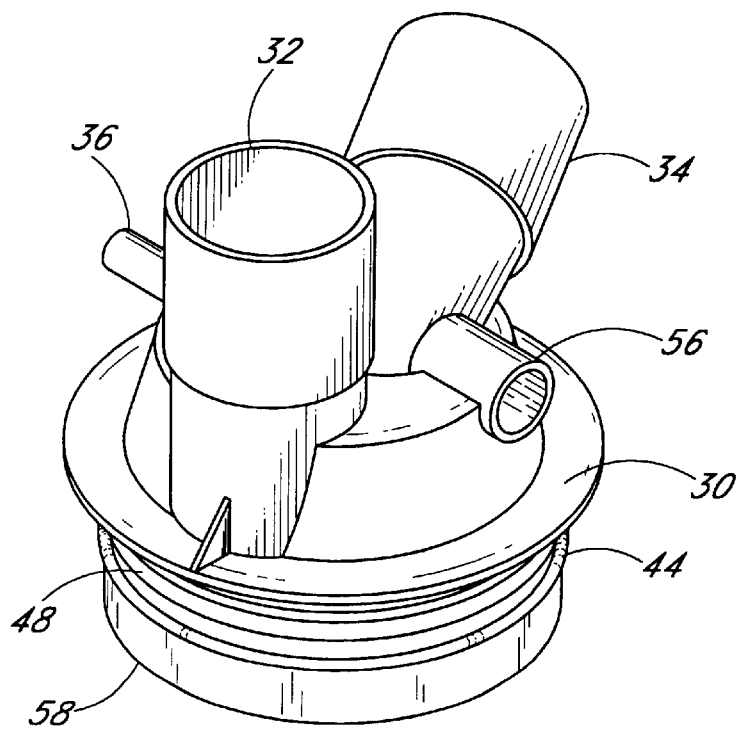

FIG. 2 is top plan view of the cartridge of FIG. 1;

FIG. 3 is a bottom plan view of the cartridge of FIG. 1;

FIG. 4 is a side view, partially in section showing a cartridge of FIG. 1 installed and positioned in a humidifier container cavity;

FIG. 5 is a sectional view taken along line A—A of FIG. 4;

FIG. 6 is a bottom view of a lid secured in the cartridge and on the humidifier container as shown in FIG. 4; and FIG. 7 is a perspective view of the lid shown in FIG. 6.

DETAILED DESCRIPTION OF THE PREFERRED EMBODIMENT

FIGS. 1–3 illustrate a preferred embodiment of the cartridge for reducing compliance in a humidifier according to the invention. The shape of the cartridge is important in that it must be suitable for being received in or installed in the interior cavity of the humidifier chamber in which it is to be used. Observing also FIG. 4, as well as the aforesaid patents, and particularly U.S. Pat. No. 4,674,494, where the humidifier container is an elongated cylindrical container, the cartridge to be used is also preferably elongated, having a shape like that shown in FIG. 1. Such a shape as well as the dimensions of the cartridge, including the cross-section shape, configuration and diameter are such that it is capable of being readily installed and positioned in the interior cavity of the container and displacing the desired amount of space in the humidifier cavity. Accordingly, although the shape of the preferred embodiment of the present invention is elongated and generally cylindrical so that it is suitable for use in an elongated and generally cylindrical humidifier cavity, other cartridge shapes may be used where the humidifier cavity is of a different shape and/or size so as to be effective in achieving the same improved and reduced compliance as achieved by the preferred embodiment described herein and shown in the drawings.

Referring again to FIGS. 1–3, cartridge 10 comprises an elongated hollow shell 11, along the length of which are channels 21, 23 and 25 forming channel spaces or paths between the cartridge exterior and the interior surface of the humidifier chamber. The cartridge is provided with a gas inlet port 13 and a gas outlet port 15 defined by annular collars 12 and 14, respectively. These collars are formed at the upper end of the cartridge where they are in communication with gas inlet and outlet ports extending outwardly of the humidifier assembly. Gas inlet port 13 communicates with space 22 in channel 21 and gas outlet port 15 communicates with space 24 along channel 23. A third port 17 communicates with space 26 along channel 25, which port is defined by annular collar 16, also formed at the upper end of the cartridge. Third port 17 and channel 25 are for the purpose of receiving a water level control pipe which communicates via port 17 with a water container reservoir for supplying water to the humidifier chamber as will be discussed hereinafter.

The humidifier assembly of the invention includes a cap member or lid 30 illustrated in FIGS. 4, 6 and 7 which sealingly engages with the upper end of humidifier container 40. The lid 30 includes gas inlet fitting 32 and gas outlet fitting 34 for being connected to respiratory or ventilator circuit tubing (not shown). As shown in FIG. 7, a temperature monitor port 56 is provided on gas outlet fitting 34 for receiving a thermometer or temperature sensor device for monitoring the gas temperature of the humidified respiratory gas mixture delivered from the humidifier to a patient inspiratory tubing limb. As previously disclosed, the humidifier container is placed in a heater for heating the water present in the humidifier chamber to provide heated molecular humidity to the patient via gas outlet 34. It is preferred to monitor the temperature of the heated and humidified gas delivered via the gas outlet port to the patient as it leaves the humidifier assembly. The lid also is provided with a gas vent port adapter 36 for being attached to a tube extending between the lid and the upper end of a water reservoir, as illustrated in U.S. Pat. No. 4,500,480 and 4,674,494, the description of which are incorporated herein by reference.

Referring to FIG. 6, on the interior of the lid 30 are annular sleeves 52, 54 and 46 which extend along the interior of the lid from the respective ports. Sleeve 52 extends from gas inlet fitting 32, sleeve 54 extends from gas outlet fitting 34, and sleeve 46 communicates with gas vent pipe 36. The three sleeves are oversized relative to the three collars illustrated in FIGS. 1 and 2. Thus, the interior diameter of sleeves 52 and 54 are slightly larger than the exterior diameter of collars 12 and 14, while the interior diameter of sleeve 46 is slightly oversized relative to the interior diameter of collar 16. Such relative sizes allow the lid to be secured on the humidifier assembly with collars 12, 14 and 16 extending into sleeves 52, 54 and 46, respectively. In that manner, with the lid secured on the humidifier container, the collars extend into the sleeves thereby providing full communication of the gas inlet port 13 with gas inlet fitting 32, gas outlet port 15 with gas outlet fitting 34 and port 17 with gas vent pipe 36.

Lid 30 is also provided with an annular skirt 58 along which is positioned an O-ring 44. Observing also FIG. 4, the diameter of skirt 58 is such that it fits inside of the upper end of the humidifier container 40, with O-ring 44 sealingly engaging the interior container surface to provide a gas and water-tight seal between the components. The lid also preferably includes a lip 48 which acts as a stop as the lid is positioned on the upper end of the humidifier container when the two components are filly assembled. The interior surface of skirt 58 is also preferably tapered so as to provide a force-fit engagement of the upper end of the cartridge when it is assembled or secured to the lid. A water level control pipe 35 is secured in sleeve 46, the sleeve preferably being slightly tapered so as to engage the upper end of pipe 35 in a force-fit assembly. At the lower end of pipe 35 is a water level control port 38, the position of which will determine and control the amount of water delivered from the reservoir via a pipe or tube, not shown, attached to water supply inlet nipple 50, again as illustrated in U.S. Pat. Nos. 4,500,480 and 4,674,494, the descriptions of which are incorporated herein by reference. However, the humidifier assembly of the invention is not limited to one in which the water level is to be so controlled, and instead, may be used in a standard humidifier in which the water level is maintained and corresponds to the water level in the reservoir. In standard humidifier columns, typically used in most adult ventilatory applications the compressible volume, i.e., the volume of gas within the humidifier corresponds to the water level in the reservoir and is gradually depleted by evaporation of the water in the humidifier.

Observing again FIGS. 1 and 2, the upper end of the cartridge is provided with a rib 31 which engages and preferably has a sealing force-fit with the tapered interior surface of skirt 58 as the cartridge is urged upwardly into the lid. The interior cavity of the cartridge shown is open at the upper end of the cartridge, with the bottom end of the cartridge being closed. With collars 12, 14 and 16 extending into lid sleeves 52, 54 and 46, respectively, once the cartridge is fully assembled and secured within the lid, the interior cavity of the cartridge is substantially isolated from the humidifier chamber and provides a dead-gas space which does not substantially receive or deliver respiratory gas or gas delivered to and from the humidifier. Thus, when the cartridge is installed and assembled in the humidifier, it effectively displaces its volume within the humidifier cavity.

Observing FIG. 4 and also FIG. 5, the relationship of the cartridge installed in the humidifier cavity may be observed. With the apparatus fully assembled, and attached to a ventilator circuitry, not shown, during operation, respiratory gas from a ventilator is forced into gas inlet fitting 32, through gas inlet port 13, along channel space 22 and is exposed to heated water within the interior cavity of the humidifier container. The humidified respiratory gas is forced out of the assembly via channel space 24, through gas outlet port 15 and outlet fitting 34 to the patient. Humidification of the respiratory gas may be improved by using a wicking material such as an absorbent paper 41 shown in FIG. 5, and as illustrated and disclosed in U.S. Pat. No. 4,674,494, the description of which is incorporated herein by reference. However, other wicking devices or components or other means for improving the humidification of the respiratory gas within the chamber may also be used. Again, the shape and size of the cartridge are important for being accommodated and secured within the humidifier container interior cavity. The size of the cartridge is important only in that it occupies or displaces a significant or substantial amount of the gas space within the interior cavity thereby correspondingly reducing the gas volume of the cavity and the compliance of the humidifier as previously described. By so reducing compliance, the amount of gas which must be compressed, moved, heated and humidified within the humidifier is correspondingly reduced, thereby substantially improving the efficiency and overall functioning of the apparatus. Thus, with substantially reduced compliance as provided by the present invention resulting from reduction of between about 20% and about 80% of the volume of the humidifier cavity, a reduction of pressure needed to drive respiratory gas through the humidifier is achieved as compared to present humidifiers. Preferably, the cartridge displacement is between about 50% and about 80% of the humidifier cavity volume. In a specific example, the apparatus shown and described herein, the compressible volume of a 405 ml humidification chamber (Hudson RCI humidifier #385-20 and 385-30) was reduced to 105 ml by incorporation of the cartridge substantially as shown in FIGS. 4 and 5. Moreover, the compliance in ml/cm $H_2O$ at pressures between 5 and 60 cm $H_2O$ was reduced by between about 30% and about 60%. More specifically, at pressures of 5, 10 and 15 cm $H_2O$ the compliance of the aforesaid humidification chamber was reduced from 0.3 to 0.2 ml/cm $H_2O$ and at pressures above 15 cm (20, 30, 40 and 60 cm $H_2O$) from 0.4 to 0.2 ml/cm $H_2O$. Such a reduction in compliance is particularly advantageous and important for mechanical ventilation of pediatric, infant and neonatal patients, where relatively low or reduced mechanical ventilator pressures are critical as are the pressure ranges to which the patients are exposed.

What is claimed is:

1. A humidifier assembly for respiratory therapy comprising:

a container having a cavity for holding water, a feed port for directing water into said cavity, a gas inlet port for directing respiratory gas into said cavity, a gas outlet port for directing said respiratory gas from said cavity, and a cartridge secured in said cavity, the interior of said cartridge being substantially isolated from said cavity and wherein said cartridge displaces between about 20% and about 80% of the volume of said cavity.

2. The humidifier assembly of claim 1, including a water level control pipe extending into said cavity having a first end in open communication with the interior of said cavity and a second end communicating exteriorly thereof.

3. The humidifier assembly of claim 2 wherein said cartridge includes an exterior channel along which said water level control pipe extends.

4. The humidifier assembly of claim 1 wherein said cartridge comprises a substantially hollow shell.

5. The humidifier assembly of claim 4 wherein said cartridge includes first and second channels formed along the exterior of said shell, one of said channels in communication with said gas inlet port and another of said channels in communication with said gas outlet port.

6. The humidifier assembly of claim 5 wherein said cartridge includes a third channel formed along the exterior of said shell.

7. The humidifier assembly of claim 2 wherein said cartridge includes first and second channels formed along the exterior of said shell, one of said channels in communication with said gas inlet port and another of said channels in communication with said gas outlet port, and a third channel formed along the exterior of said shell and along which said water level control pipe extends.

8. The humidifier assembly of claim 1 including a cap member secured at an upper end of said container and a substantially gas tight seal extending between said cap member and said container, wherein said gas inlet port comprises a gas inlet fitting including a pipe extending from said cap member and said gas outlet port comprises a gas outlet fitting including a pipe extending from said cap member.

9. The humidifier assembly of claim 8 wherein said cartridge comprises a substantially hollow shell.

10. The humidifier assembly of claim 9 wherein said cartridge includes first and second channels formed along the exterior of said shell, one of said channels in communication with said gas inlet port and another of said channels in communicating with said gas outlet port.

11. The humidifier assembly of claim 1 wherein said feed port includes a fluid inlet pipe formed on one end of said container, and wherein said gas inlet port and said gas outlet port are located at one end of said container and said fluid inlet pipe at an opposite end thereof.

12. The humidifier assembly of claim 2 wherein said gas inlet port and said gas outlet port are provided at one end of said cartridge.

13. The humidifier assembly of claim 12 wherein said cartridge comprises a hollow shell and includes first and second channels formed along the exterior of said shell, one of said channels in communication with said gas inlet sort and another of said channels in communication with said gas outlet port.

14. The humidifier assembly of claim 13 wherein said feed port comprises a fluid inlet pipe extending from one end of said container, opposite said gas inlet port and said gas outlet port.

15. The humidifier assembly of claim 14 including a cap member secured at an upper end of said container and a substantially gas tight seal extending between said cap member and said container, wherein said gas inlet port comprises a gas inlet pipe extending from said cap member and said gas outlet port comprises a gas outlet pipe extending from said cap member.

16. The humidifier assembly of claim 15 wherein said cartridge includes first and second channels formed along the exterior of said shell, one of said channels in communication with said gas inlet port and another of said channels in communication with said gas outlet port.

17. The humidifier assembly of claim 16 wherein said cartridge includes a third channel formed along the exterior of said shell.

18. The humidifier assembly of claim 15 wherein said cartridge includes first and second channels formed along the exterior of said shell, one of said channels in communication with said gas inlet port and another of said channels in communication with said gas outlet port and a third channel formed along the exterior of said shell and along which said water level control pipe extends.

19. The humidifier assembly of claim 18 wherein said feed port includes a fluid inlet pipe formed on one end of said container, and wherein said gas inlet port and said gas outlet port are located at one end of said container and said fluid inlet pipe at an opposite end thereof.

20. The humidifier assembly of claim 19 wherein said cap member includes a gas vent pipe extending therefrom, said gas vent pipe communicating with said water level control pipe.

21. The humidifier assembly of claim 20 including a water supply reservoir for supplying water to said container, a first tube extending between said gas vent pipe and an upper end of said water supply reservoir, and a second tube extending between said fluid inlet pipe and a lower end of said water supply reservoir.

22. The humidifier assembly of claim 21 including a heater for heating water in said container, said heater having a compartment for receiving said container, and wherein said container is secured in said compartment.

23. A cartridge for reducing the compliance in a humidifier chamber for humidifying respiratory gas comprising a hollow shell having a shape capable of being received in said chamber and having a size for displacing between about 20% and about 80% of the volume of said chamber, said hollow shell having a closed lower end and an open upper end and whereby the interior of said cartridge comprises a cavity for being substantially isolated from said humidifier chamber.

24. The cartridge of claim 23 wherein said hollow shell has one or more channels formed along the exterior thereof.

25. The cartridge of claim 24 including one or more ports on said cartridge for directing gas to or from said one or more channels.

26. The cartridge of claim 25 wherein one or more of said one or more ports comprises a collar.

27. The cartridge of claim 23 wherein said hollow shell comprises an interior cavity and wherein said cartridge includes a cover for sealing said interior cavity.

28. The cartridge of claim 24 wherein said hollow shell comprises an interior cavity and wherein said cartridge includes a cover for sealing said interior cavity.

29. The cartridge of claim 25 wherein said hollow shell comprises an interior cavity and wherein said cartridge includes a cover for sealing said interior cavity.

30. The cartridge of claim 28 wherein said cover includes one or more ports for directing gas to or from said one or more channels.

31. The cartridge of claim 27 wherein said hollow shell includes a first channel and a second channel formed along the exterior thereof, and wherein said cover includes a first port in communication with said first channel and a second port in communication with said second channel.

32. The cartridge of claim 31 wherein said first channel and said first port and second channel and said second port are sealed from communicating with said interior cavity.

33. The cartridge of claim 31 wherein said hollow shell includes a third channel formed along the exterior thereof, and wherein said cover includes a third port in communication with said third channel.

34. The cartridge of claim 32 wherein said hollow shell includes a third channel formed along the exterior thereof, and wherein said cover includes a third port in communication with said third channel and where said third channel and said third port are sealed from communicating with said interior cavity.

35. In a process for humidifying respiratory gas supplied to a patient from a mechanical ventilator by directing a column of said gas through a humidifier comprising a water containing cavity, a method of reducing the compliance of said humidifier comprising providing a cartridge having a hollow interior wherein said cartridge is capable of displacing between about 20% and about 80% of the volume of said cavity, and installing said cartridge in said cavity whereby the hollow interior thereof is substantially isolated from the cavity.

36. A method of claim 35 wherein said cartridge is provided with a first channel communicating with a gas inlet port and a second channel communicating with a gas outlet port, and wherein a column of said gas is directed along said first channel and exposed to water in said cavity and is directed therefrom along said second channel to said gas outlet port.

37. The humidifier assembly of claim 8 wherein said gas outlet fitting includes a temperature monitor port for receiving a temperature sensor for monitoring the temperature of humidified gas directed from said cavity.

38. The humidifier assembly of claim 11 wherein said gas outlet port comprises a fitting having a temperature monitor port for receiving a temperature sensor for monitoring the temperature of humidified gas directed from said cavity.

39. The humidifier assembly of claim 12 wherein said gas outlet port comprises a fitting having a temperature monitor port for receiving a temperature sensor for monitoring the temperature of humidified gas directed from said cavity.

40. The humidifier assembly of claim 37 including a water level control pipe extending into said cavity, and wherein said cap member includes a gas vent pipe extending therefrom, said gas vent pipe communicating with said water level control pipe.

41. The humidifier assembly of claim 8 where in said cartridge comprises a substantially hollow shell having an open upper end communicating with said cap member and a closed lower end.

* * * * *

UNITED STATES PATENT AND TRADEMARK OFFICE
CERTIFICATE OF CORRECTION

PATENT NO.    : 6,050,552
DATED         : April 18, 2000
INVENTOR(S)   : Loescher et al.

It is certified that error appears in the above-identified patent and that said Letters Patent is hereby corrected as shown below:

Column 3,
Line 38, replace "filly" with -- fully --.

Signed and Sealed this

Twenty-third Day of September, 2003

JAMES E. ROGAN
*Director of the United States Patent and Trademark Office*